(12) United States Patent
Molho et al.

(10) Patent No.: US 8,202,486 B2
(45) Date of Patent: Jun. 19, 2012

(54) PINCHING CHANNELS FOR FRACTIONATION OF FRAGMENTED SAMPLES

(75) Inventors: Josh Molho, Oakland, CA (US); Hui Xu, Palo Alto, CA (US); Jorge J. Zaninovich, Walnut Creek, CA (US)

(73) Assignee: Caliper Life Sciences, Inc., Alameda, CA (US)

( * ) Notice: Subject to any disclaimer, the term of this patent is extended or adjusted under 35 U.S.C. 154(b) by 88 days.

(21) Appl. No.: 12/843,557

(22) Filed: Jul. 26, 2010

(65) Prior Publication Data

US 2011/0036411 A1    Feb. 17, 2011

Related U.S. Application Data

(60) Provisional application No. 61/233,392, filed on Aug. 12, 2009, provisional application No. 61/266,030, filed on Dec. 2, 2009.

(51) Int. Cl.
*C12M 1/36* (2006.01)
*C12M 1/34* (2006.01)

(52) U.S. Cl. ............ 422/255; 422/50; 422/82; 422/549; 204/450; 204/600; 137/1; 137/861; 435/286.2; 435/287.1; 436/161

(58) Field of Classification Search .................. None
See application file for complete search history.

(56) References Cited

U.S. PATENT DOCUMENTS

| 4,608,147 | A | 8/1986 | Clad |
| 5,140,161 | A | 8/1992 | Hillman et al. |
| 5,827,418 | A | 10/1998 | Haven et al. |
| 6,270,641 | B1 | 8/2001 | Griffiths et al. |
| 6,485,625 | B1 | 11/2002 | Simpson et al. |
| 6,506,609 | B1 | 1/2003 | Wada et al. |
| 7,419,784 | B2 | 9/2008 | Dubrow et al. |
| 2002/0127736 | A1 | 9/2002 | Chou et al. |
| 2003/0044832 | A1 | 3/2003 | Blankenstein |

(Continued)

FOREIGN PATENT DOCUMENTS

WO    0151918 A1    7/2001

(Continued)

OTHER PUBLICATIONS

Effenhauser et al., "Manipulation of sample fractions on a capillary electrophoresis chip." Analytical Chemistry, vol. 67, No. 13, pp. 2284-2287, Jul. 1, 1995; American Chemical Society, US.

(Continued)

*Primary Examiner* — In Suk Bullock
*Assistant Examiner* — Timothy G Kingan
(74) *Attorney, Agent, or Firm* — Cardinal Law Group

(57) ABSTRACT

The invention provides a device, system, and method for isolating one or more sample components of a sample material following separation of the sample material into a plurality of sample components. The device includes first and second pinching channels, a separation channel extending between the first and second pinching channels, a collection leg that includes a collection well, and a waste leg, all of which are in fluid communication with a switching region. In the method, a sample material is separated into a plurality of separated components in the device. and one or more of the separated components are isolated in the collection well. The separated components are constrained and elongated in the switching region by first and second buffer streams.

13 Claims, 6 Drawing Sheets

U.S. PATENT DOCUMENTS

| | | | |
|---|---|---|---|
| 2004/0224380 A1* | 11/2004 | Chou et al. | 435/29 |
| 2005/0109410 A1* | 5/2005 | Gilbert et al. | 137/827 |
| 2005/0205427 A1 | 9/2005 | Boschetti et al. | |
| 2008/0014589 A1* | 1/2008 | Link et al. | 435/6 |
| 2008/0261295 A1* | 10/2008 | Butler et al. | 435/286.5 |
| 2010/0126862 A1 | 5/2010 | Sabin et al. | |

FOREIGN PATENT DOCUMENTS

| | | |
|---|---|---|
| WO | 03013703 A1 | 2/2003 |
| WO | 2010042766 A1 | 4/2010 |

OTHER PUBLICATIONS

Griffiths et al., "Low-dispersion turns and junctions for microchannel systems." Analytical Chemistry, vol. 73, No. 2, pp. 272-278, Jan. 15, 2001; American Chemical Society, US.

Jacobson et al., "Electrokinetic focusing in microfabricated channel structures." Analytical Chemistry, vol. 69, No. 16, pp. 3212-3217, Aug. 15, 1997; American Chemical Society, US.

Li et al., "Design, simulation, and optimization of a miniaturized device for size-fractioned DNA extraction." Electrophoresis, vol. 28, pp. 4661-4667, 2007; Wiley-VCH Verlag GMBH & Co. KGaA, Weinheim.

Lin et al., "Selective extraction of size-fractionated DNA samples in microfabricated electrophoresis devices." Journal of Chromatography A, vol. 1010, pp. 255-268, 2003; Elsevier BV, Netherlands.

Zalewski et al., "Electrophoretic sorting and collection of fractions for preparative capillary electrophoresis on a chip." Lab on a Chip, vol. 8, No. 5, pp. 801-809, 2008; Royal Society of Chemistry, UK.

* cited by examiner

PINCHING CHANNELS FOR FRACTIONATION OF FRAGMENTED SAMPLES

CROSS-REFERENCE TO RELATED APPLICATIONS

This application claims the benefit of U.S. Provisional Application No. 61/233,392 filed Aug. 12, 2009, and U.S. Provisional Application No. 61/266,030 filed Dec. 2, 2009, the disclosures of which are herein incorporated by reference.

TECHNICAL FIELD

The present disclosure is in the field of devices and systems for separation and isolation of sample components and method for their use. In particular, described herein are systems, devices, and methods for isolating one or more sample components of a sample material following separation of the sample material into a plurality of sample components.

BACKGROUND OF THE INVENTION

Separations-based analyses are a prominent part of biological research, allowing one to characterize different biological samples, reaction products and the like. Examples of some of the more prevalent separations-based analyses include electrophoretic separations of macromolecular species, e.g., proteins and nucleic acids. Electrophoresis, e.g., capillary electrophoresis, has been established as a highly effective method for separating macromolecular species in order that they might be further characterized. Protein and nucleic acid molecules are two major examples of molecular species that are routinely fractionated and characterized using electrophoretic systems.

Both microfluidic and macrofluidic devices have been applied in separations-based analyses. Examples of novel microfluidic devices and methods for use in the separation of molecular, and particularly macromolecular species by electrophoretic means are described in U.S. Pat. Nos. 5,958,694, 6,032,710, and 7,419,784, for example, the entire contents of which are incorporated by reference herein. In such devices, the sample containing the macromolecular species for which separation is desired is placed in one end of a separation channel located in a microfluidic substrate and a voltage gradient is applied along the length of the channel. As the sample components are electrophoretically transported along the length of the channel and through the separation (sieving) matrix disposed therein, those components are resolved. The separated components are then detected at a detection point along the length of the channel, typically near the terminus of the separation channel downstream from the point at which the sample was introduced. Following detection, the separated components are typically directed to a collection reservoir/well in the device (or to an external device such as a multiwell plate via a capillary pipettor, for example) for subsequent extraction or disposal.

In many situations, it is desirable to extract selected fragments of interest, such as DNA fragments, following the separation of the fragments into bands in the separation matrix for further processing or analysis, e.g., restriction enzyme modification, T4 ligation, PCR amplification, mass spectroscopy, or polynucleotide kinase reactions. The typical process used by laboratory researchers for extracting and isolating selected DNA fragments of interest (and other desired nucleic acid and protein fragments) from a separation matrix (such as an agarose gel) involves excising the desired fragments from the separation matrix and then extracting and purifying the excised fragment(s). First, the separated fragments are stained and illuminated by shining ultraviolet (UV) light on the fragments to visualize the separated bands. A razor blade is then used to manually cut above and below each fragment of interest so that one or more slices of the sieving can be removed. Then the DNA is extracted from the removed slices using various solutions and heating to dissolve the sieving matrix. The DNA can be further purified by standard solid phase extraction (binding the DNA to a solid surface such as glass followed by washing and finally elution). The recovered DNA can then be used for further processing or analysis. This extraction process, however, is time consuming, laborious and potentially damaging to the DNA (e.g., nicking of the DNA can occur if the DNA is exposed to ultraviolet light too long while the fragments of interest are being illuminated for excision).

Thus, in performing separations-based analyses, it would be desirable to be able to also isolate or extract one or more of the separated components in the device itself for further analysis or processing. The recovered or isolated fragments could then be used for a variety of different processes including, for example, the following: amplification using polymerase chain reaction (PCR); ligation reactions for cloning small to medium-sized strands of DNA into bacterial plasmids, bacteriophages, and small animal viruses to allow the production of pure DNA in sufficient quantities to allow its chemical analysis; adapter ligation used in high-throughput sequencing; reactions to dissolve a separated protein or nucleic acid component in a suitable matrix for further analysis by a mass spectrometer using, for example, Matrix-Assisted Laser Desorption Ionization (MALDI); binding reactions to bind a labeling agent to one or more separated protein or nucleic acid components for further analysis; or other similar post-detection processes. In addition, in the case of PCR samples, it is important to be able to separate smaller dimer and primer molecules from the main nucleic acid fragments in the sample and then isolate and collect the main nucleic acid fragments for further analysis or processing, while directing the smaller primer and dimer components to a waste reservoir/cell for removal and subsequent disposal.

Thus, it would be advantageous to provide improved devices, systems and methods for use in separating sample materials into different sample components or fragments and then isolating one or more of the sample components for further processing or analysis.

SUMMARY OF THE INVENTION

One aspect of the present invention is a device for isolating one or more sample components of a sample material following separation of the sample material into a plurality of sample components. The device comprises first and second pinching channels, each pinching channel having a first end and a second end; a separation channel extending between the first and second pinching channels, the separation channel having a first end and a second end; a collection leg having a first end and a second end; a collection well disposed in the collection leg between the first and second ends of the collection leg; a waste leg having a first end and a second end; and a switching region having an inlet end and an outlet end. The second end of each of the first pinching channel, the second pinching channel, and the separation channel are in fluid communication with the inlet end of the switching region, and the first end of the collection leg and the first end of the waste leg are in fluid communication with the outlet end of the switching region.

Another aspect of the present invention is a system for isolating one or more sample components of a sample material following separation of the sample material into a plurality of sample components. The system comprises a first device, a detector in sensory communication with the device, a fluid direction system, and a processor operably coupled to the detector and the fluid direction system. The first device comprises first and second pinching channels, a separation channel extending between the first and second pinching channels, a collection leg including a collection well disposed between a first end and a second end of the collection leg, and a waste leg. The first and second pinching channels and the separation channel are in fluid communication with an inlet end of the switching region, and the collection leg and the waste leg are in fluid communication with an outlet end of the switching region.

Yet another aspect of the present invention is a method for isolating one or more sample components of a sample material following separation of the sample material into a plurality of sample components. The method comprises loading a sample material into a loading well in fluid communication with a separation channel of a device; separating the sample material into a plurality of separated components in the separation channel, the separated components forming a stream; transporting the stream of separated components into a switching region of the device; transporting first and second buffer streams into the switching region on either side of the component stream such that the first and second buffer streams constrain and elongate the component stream as it is transported through the switching region; directing a first portion of the stream of separated components, a first portion of the first buffer stream and a first portion of the second buffer stream out of the switching region and into a waste leg of the device; directing a second portion of the stream of separated components, a second portion of the first buffer stream and a second portion of the second buffer stream out of the switching region and into a collection leg of the device; directing a third portion of the stream of separated components, a third portion of the first buffer stream and a third portion of the second buffer stream out of the switching region and into the waste leg of the device; and collecting a separated component from a collection well disposed in the collection leg.

The aforementioned and other features and advantages of the invention will become further apparent from the following detailed description of the presently preferred embodiments, read in conjunction with the accompanying drawings, which are not to scale. The detailed description and drawings are merely illustrative of the invention, rather than limiting, the scope of the invention being defined by the appended claims and equivalents thereof.

DETAILED DESCRIPTION OF THE PRESENTLY PREFERRED EMBODIMENTS

Figure 1:
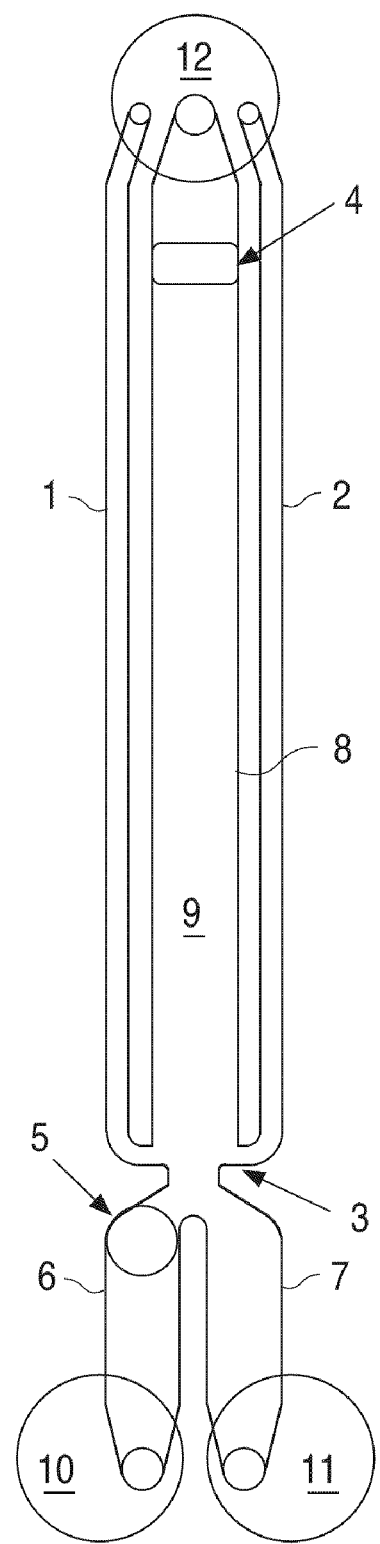
FIG. 1 is a schematic illustration of a device for isolating one or more sample components of a sample material following separation of the sample material into a plurality of sample components, in accordance with the present invention.

One aspect of the present invention is a device for isolating one or more sample components of a sample material following separation of the sample material into a plurality of sample components. One embodiment of the device, in accordance with the present invention, is illustrated in FIG. 1. The illustrated device comprises first and second pinching channels 1 and 2, a switching region 3, a loading well 4, a collection well 5, a collection leg 6, a waste leg 7, a separation channel 8, a sieving matrix 9, and reservoirs 10-12. In the present embodiment, reservoirs 10 and 11 are waste reservoirs, while reservoir 12 is a buffer reservoir.

As seen in FIG. 1, pinching channels 1 and 2 extend from reservoir 12 to switching region 3. Separation channel 8 also extends from reservoir 12 to switching region 3 and is positioned between pinching channels 1 and 2. The three channels merge at the inlet end of switching region 3. By having pinching channels 1 and 2 join separation channel 8 just above the switching region, little diffusion of the sample into the buffer streams occurs. Separation channel 8 includes a loading well 4 that is open to the external environment to permit a sample to be deposited into the loading well manually using, for example, a pipettor, or a sample may be deposited by an automated sample transfer device.

Figure 2:
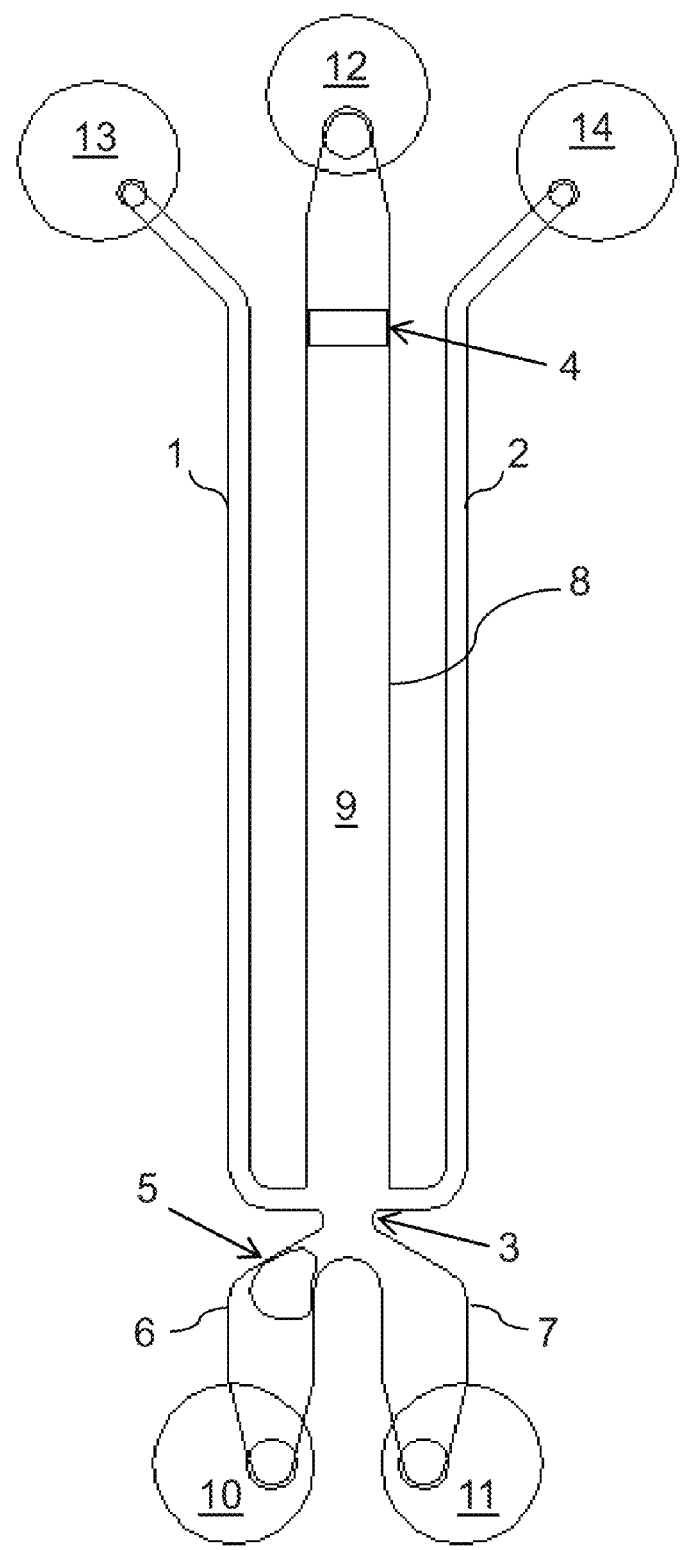
FIG. 2 is a schematic illustration of another device for isolating one or more sample components of a sample material following separation of the sample material into a plurality of sample components, in accordance with the present invention.

Legs 6 and 7 extend from the outlet end of switching region 3 to reservoirs 10 and 11, respectively. As seen in FIG. 1, collection well 5 is positioned in collection leg 6. The collection well may be positioned anywhere in the collection leg between switching region 3 and reservoir 10. Positioning the collection well nearer to the switching region than to the reservoir may permit collection of a narrower, i.e., more precisely selected, band of the separated sample material. A larger collection well may permit collection of a broader band. Collection well 5 is open to the external environment to permit removal of the isolated sample component(s) from the device. Collection well 5 may be circular as seen in FIG. 1 or may be any other shape that facilitates collecting the isolated sample component(s). For example, a free-form shape is shown in FIG. 2. While the collection well is shown in leg 6 in the illustrations, it may alternatively be positioned in leg 7 in another embodiment. In this alternative embodiment, leg 6 would then be the waste leg, and leg 7 would be the collection leg.

Separation channel 8 may include a sieving matrix 9 to facilitate electrophoretic separation of a sample within the separation channel. The sieving matrix may be, for example, agarose or a cross-linked gel. Pinching channels 1 and 2, switching region 3, legs 6 and 7, and reservoirs 10-12 may also include the sieving matrix, although reservoirs 10-12 are not completely filled with the sieving matrix and additionally contain a buffer. Loading well 4 and collection well 5 do not include the sieving matrix in order to facilitate introduction and withdrawal of sample materials. In alternative embodiments, the device may include a sieving matrix in only some or none of pinching channels 1 and 2, switching region 3, legs 6 and 7, separation channel 8 and reservoirs 10-12.

Switching region 3 may be a simple intersection of the channels entering and exiting the region, or the switching region may be extended to form a channel. Switching region 3 is shown as a narrowed "neck" in FIGS. 1 and 2 (i.e., the cross-sectional dimension [width] of the separation channel is shown as being greater than the cross-sectional dimension [width] of the switching region). Other geometries are possible. The narrowed switching region is desirable because it both increases the electric field and therefore the migration velocity within the region and helps to prevent bubbles being trapped in a separation matrix during filling of the device. However, as will be discussed further below, the switching region need not be substantially narrowed for the electric field to be increased within the separated sample in the switching region because the sample stream is "pinched," i.e., constrained or contained and thereby elongated, by buffer transported into the switching region from the two pinching channels, increasing the current density (and therefore the electric field) and creating a faster electrophoretic velocity in the sample material within the switching region. Pinching of the sample stream can be seen in FIG. 3, where the sample stream appears light and buffer streams appear dark at the switching region.

Figure 4:
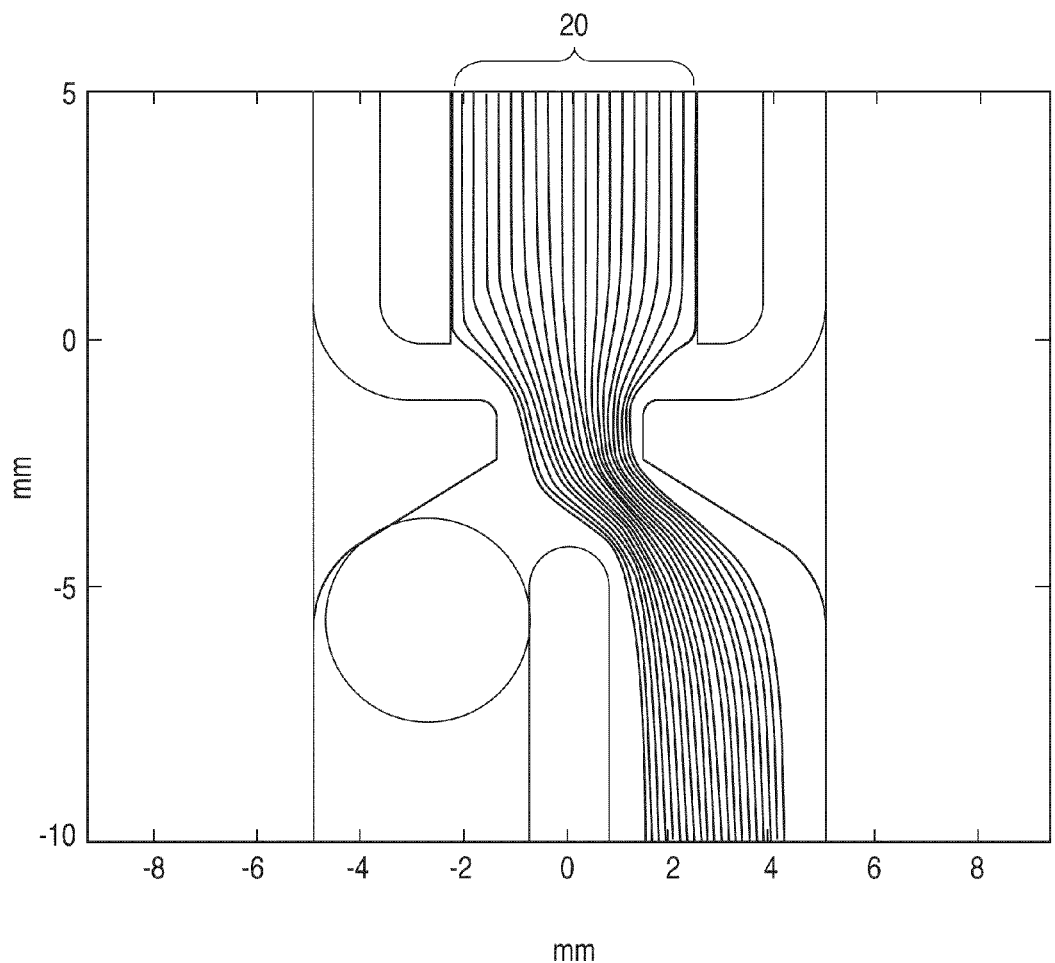
FIG. 4 is a schematic illustration of a portion of the device of FIG. 1 showing stream lines achieved using the pinching channels of the device.
Figure 5:
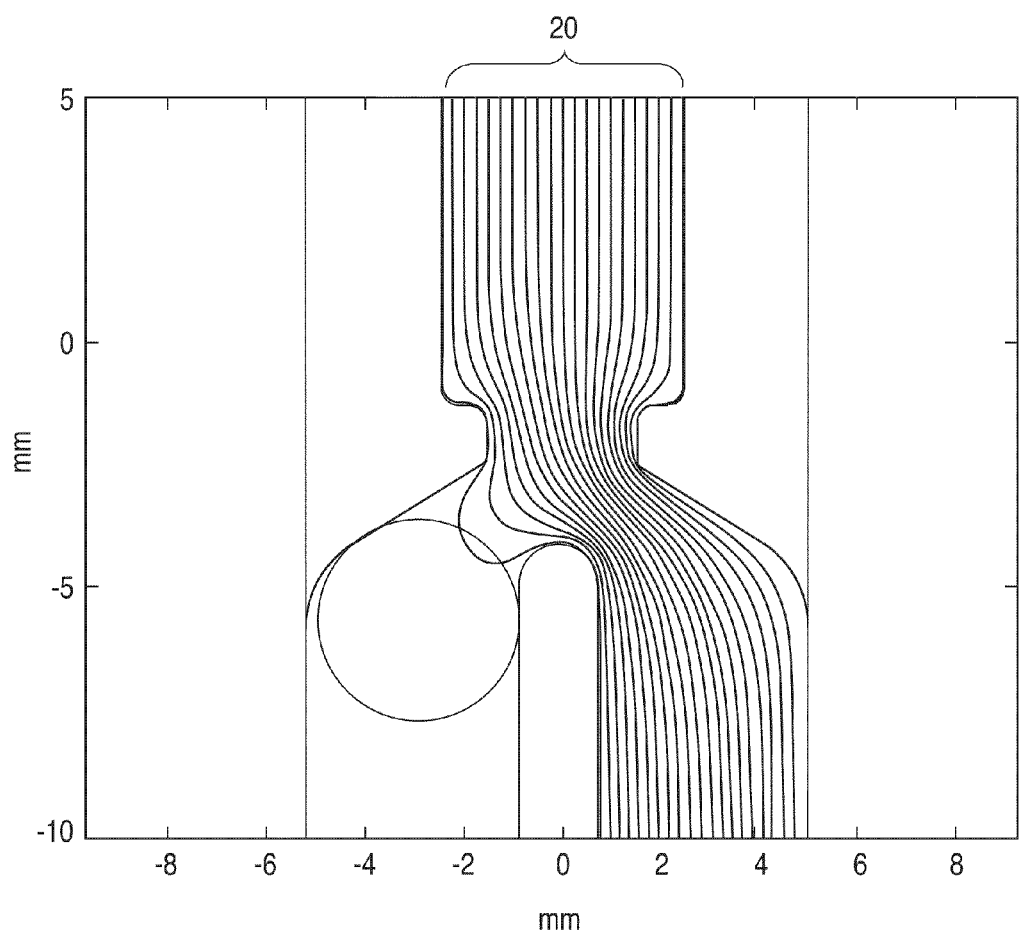
FIG. 5 is a schematic illustration of a portion of a device without pinching channels showing stream lines achieved without the benefit of the pinching channels of the device of FIG. 1.

Pinching of the sample can also be seen in FIG. 4, which models transport of sample materials through a portion of the device of FIG. 1. As can be seen by the stream lines illustrated at 20 in FIG. 4, the entire sample stream is directed away from collection leg 6 and collection well 5. Contrast FIG. 4 with FIG. 5, which models transport of sample materials through a portion of a device that does not include pinching channels. Stream lines 20 of FIG. 5 show that a portion of the sample stream strays into the collection leg and collection well of the device of FIG. 5, resulting in unwanted sample components being present in the collection well when pinching streams are not employed.

Another embodiment of the device, in accordance with the present invention, is illustrated in FIG. 2. Note that throughout the figures, like elements share like reference numbers. The illustrated device comprises first and second pinching channels 1 and 2, a switching region 3, a loading well 4, a collection well 5, a collection leg 6, a waste leg 7, a separation channel 8, a sieving matrix 9, and reservoirs 10-14. In the embodiment illustrated in FIG. 2, reservoirs 10 and 11 are waste reservoirs, while reservoirs 12-14 are buffer reservoirs. Refer to the discussion above for descriptions of elements 1-12. The embodiment shown in FIG. 2 differs from the embodiment shown in FIGS. 1 and 4 in that the device of FIG. 2 includes three buffer reservoirs rather than a single buffer reservoir.

In the embodiment of FIG. 1, pinching channels 1 and 2 share the same reservoir (reservoir 12) with separation channel 8. In this embodiment, the pinching ratio (the ratio of the electrical current in the separation channel to the current in the pinching channels) is controlled by the ratio of the pinching channel resistance to the separation channel resistance, resistance being a function of the geometry (e.g., width, depth, length) of the channel. Having a shared reservoir for the separation channel and the two pinching channels offers the benefit of minimizing the number of electrodes and power supplies required by the device, resulting in a highly compact device.

In the embodiment of FIG. 2, each of channels 1, 2, and 8 has its own separate reservoir, reservoirs 13, 12, and 14, respectively. By having separate reservoirs for each of the pinching channels and the separation channel, the pinching ratio can be controlled independent of the geometry of the channels. This may be accomplished by, for example, applying different voltages at the different reservoirs or controlling the current ratio between the separation channel and pinching channels directly using external hardware such as a power supply. Note that increasing the pinching ratio will provide better containment of the sample within the switching region at the cost of more current/power needed.

Either of the embodiments described above may include a detection region (not shown) within which the sample component(s) intended for collection are detected in order to switch the desired component(s) into the collection leg. Alternatively, the sample component(s) may be identified based on a known transit time through the device.

The materials of the device are chosen for their suitability for electrophoretic separations and for their inertness to the components to be separated and isolated in the device. Materials suitable for the device include, but are not limited to, glass and other ceramics, quartz, silicon, and polymeric substrates, e.g., plastics.

Another aspect of the present invention is a system for isolating one or more sample components of a sample material following separation of the sample material into a plurality of sample components. The system comprises a device such as has been described above as well as instrumentation for controlling the device. For example, the system may comprise a detector positioned in sensory communication with a detection region of the device, a processor operably coupled to the detector and to a fluid direction system that is configured to control movement of one or more sample components from the separation channel into the collection well of the collection leg based on information received from the detector. As used herein, the phrase "in sensory communication" refers to positioning of a detector such that it is operably connected to the device, i.e., capable of receiving a detectable signal from the contents of the device. In the case of optical signals, this requires only that the detector be positioned to receive the optical signal. The system may be configured to simultaneously control multiple fluidic circuits (a single fluidic circuit being shown, e.g., in FIG. 1). In such a configuration, the fluid direction system may be configured to control the movement of one or more sample components in one fluidic circuit based on information received by the detector in a parallel circuit.

Yet another aspect of the present invention is a method for isolating one or more sample components of a sample material following separation of the sample material into a plurality of sample components. The method may be carried out using a device or system such as has been described above and illustrated in FIGS. 1 and 2. The description below refers to the illustrated embodiments of the device, but the method may be varied depending on the geometry of the device used, various changes and modifications to the device being both possible and foreseen.

One or more buffers are loaded into the buffer reservoir(s). In an alternative embodiment of the method, the device may be supplied with buffer already loaded into the reservoir(s). A low-ionic strength buffer may be loaded into collection well 5 and a higher ionic strength buffer may be loaded into all other reservoirs and channels. A low ionic strength buffer may be preferred for the collection well if the isolated sample component(s) will later undergo amplification using PCR. A higher ionic strength buffer may be preferred for the reservoirs to provide additional buffering capacity. Current may be passing through these channels for extended periods, for example up to 60 minutes, and a higher buffer concentration may mitigate changes in pH within the device due to the passage of current through the device. In addition, field amplified sample stacking (FASS) will occur when a higher conductivity buffer is used in the separation channel and the input sample is loaded in a low conductivity buffer. FASS will increase the sensitivity and resolution of the separation.

A sample is deposited into the loading well, shown at 4 in FIGS. 1 and 2. The sample may be deposited manually using, for example, a pipettor, or may be deposited by an automated sample transfer device. A voltage is applied to buffer reservoir 12, and a different voltage is applied to waste reservoir 11 to electrophoretically separate the sample into a plurality of sample components in separation channel 8. Initially, no electrical connection is made to waste reservoir 10 in order to maintain zero current within collection leg 6, thereby directing the separated sample into waste leg 7 and waste reservoir 11 until a component of the sample desired for isolation and collection reaches switching region 3. Alternatively, the fluid direction system may control the voltage at waste reservoir 10 in order to maintain zero current. Note that the term "zero current" is defined herein as a current that is negligible as compared to the current in the other leg, such as a current that is less than 2% of the current in the other leg.

Figure 3:
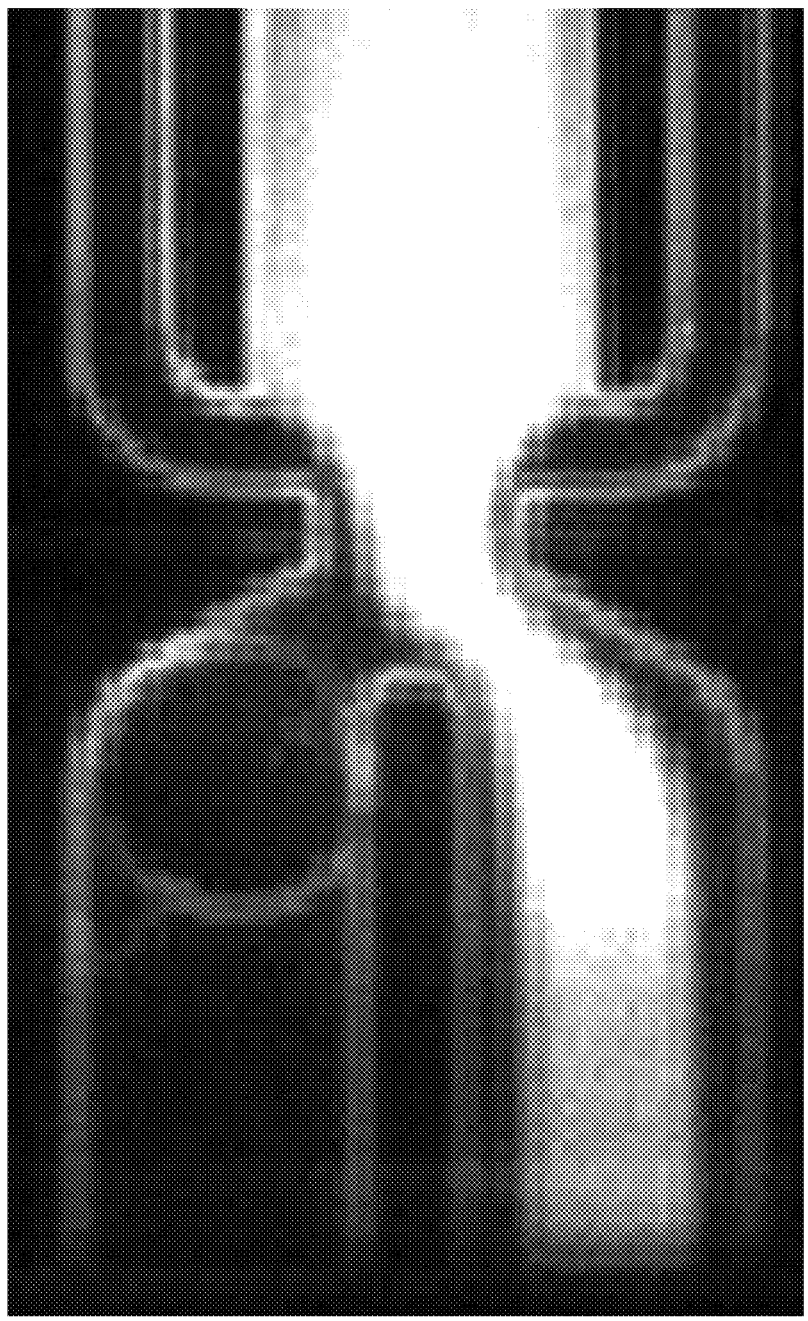
FIG. 3 is a photograph of a portion of a device in accordance with the present invention, the device shown during operation.

At the same time that the sample is being separated in separation channel 8, buffer is being transported through pinching channels 1 and 2 as a result of a voltage difference between waste reservoir 11 and the buffer reservoir connected to each of the pinching channels (reservoir 12 in FIG. 1, and reservoirs 13 and 14 in FIG. 2). As the separated sample passes through switching region 3, the buffer streams from the two pinching channels "pinch" (i.e., constrain or contain) the separated sample as seen in FIGS. 3 and 4, thereby increasing the field and creating a faster electrophoretic velocity in the sample material within the switching region. Pinching of the sample prevents leakage of the sample into the non-target leg. Leakage can be seen in FIG. 5, which illustrates a device that does not include pinching channels. Initially, the non-target leg is collection leg 6. Waste leg 7 remains the target leg until the component(s) to be isolated enter switching region 3, and the sample stream is momentarily switched, i.e., diverted, into collection leg 6, which then becomes the target leg.

Once the one or more components that are to be isolated and collected are within switching region 3, a voltage is applied to waste reservoir 10, and a zero current is maintained at waste reservoir 11. This switches the direction of the sample stream from waste leg 7 into collection leg 6. The redirection of the sample stream is timed to isolate only the desired component(s) of the sample. Once the one or more desired components are within collection leg 6 and positioned at the location of collection well 5, the sample stream is directed back into waste leg 7 and waste reservoir 11 by once again controlling zero current to waste reservoir 10 and resuming the original voltage to waste reservoir 11. Once zero current is imposed at the electrical connection to waste reservoir 10, transport into collection leg 6 stops, and the desired one or more components of the sample remain in place within collection leg 6 at the location of collection well 5. The sample component(s) may then be removed from collection well 5 manually using, for example, a pipettor, or may be withdrawn by an automated sample transfer device.

As described above, the pinching ratio of the device illustrated in FIG. 1 is controlled by the ratio of the pinching channel resistance to the separation channel resistance, resistance being a function of the geometry of the channel. The pinching ratio of the device illustrated in FIG. 2 can be controlled independently of the geometry, for example by applying different voltages at the various reservoirs or controlling the current ratio between the separation channel and pinching channels directly using external hardware such as a power supply. Increasing the pinching ratio provides better confinement of the sample at the switching region at the cost of needing more current/power.

As has been discussed previously, pinching the sample stream as it is transported into switching region 3 increases the field and creates a faster electrophoretic velocity in the sample material within the switching region as compared to that within the separation channel. The value of pinching can be readily understood when placed in context. When fractionating DNA, for example, the higher velocity decreases the number of base pairs per unit distance. That is, as the ratio of the velocity in the switching region to the velocity in the separation channel is increased, the number of base pairs within switching region 3 is decreased, in effect "stretching out" the separated sample and elongating the sample stream. This increases the precision of diverting a small band comprising the desired component(s) to collection leg 6 because the physical size of the switching intersection is in some ways equivalent to the thickness of a scalpel blade used to cut a slice containing one or more bands out of a gel. When cutting a gel, the thickness of the blade determines the minimum size slice that can be cut from the gel because it is difficult (practically impossible) to cut a slice that is thinner than the thickness of the blade. If the gel could be stretched, a more precise selection could be cut from the gel using the same size scalpel. By the same token, in the present method, increasing the pinching ratio will increase the resolution of the "cut" performed by the device. Other methods besides or in addition to increasing the pinching ratio may be used to increase the velocity at the switching region. Any method that increases either the electric field or species mobility will be effective. Such methods include (but are not limited to) the following: changing the depth of the channel at the switching region, changing or removing the sieving matrix near the switching region (so as to increase the mobility of species) or creating a step reduction in conductivity near the region.

While the sample is being separated, it is desirable to maintain the same separation field within the separation channel regardless of whether sample is being sent to the left (collection leg 6) or the right (waste leg 7). The collection well (seen at 5 in FIGS. 1 and 2) may, for example, contain buffer of a different conductivity than the running buffer, i.e., the buffer being transported through separation channel 8. As mentioned above, buffers of different conductivity may be used within the device, with a higher conductivity buffer in one or more of the channels than is present in collection well 5. Thus, the resistance could be different in the two legs and the exact value of the resistance unknown. Such uncertainty in the channel resistances means that the fluid direction system cannot maintain the same electric field in separation channel 8 when the target leg is switched. To overcome this problem, voltage may be controlled at the switching region by reading the voltage at the leg that has zero current. See FIG. 6. That is, because zero current is maintained in one leg, e.g., in leg 6, the voltage in leg 6 is the same throughout the leg, all the way up to switching region 3; therefore, reading the voltage in leg 6 becomes a way of measuring the voltage in the switching region ($V_i$). By adjusting the voltage and/or current in the other leg, leg 7, a desired $V_i$ may be maintained at the switching region.

Figure 6:
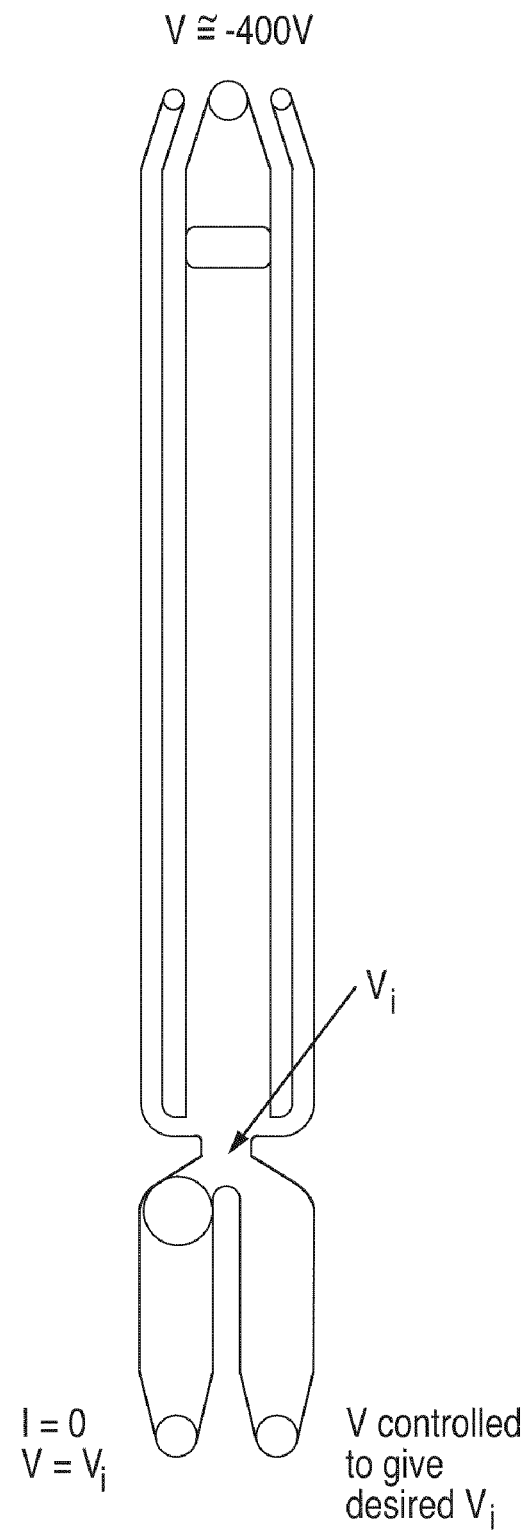
FIG. 6 is a schematic illustration of the device of FIG. 1 including information regarding a feedback control mechanism.

In this way, the voltage drop between the sample loading well (seen at 5 in FIGS. 1 and 2) and the switching region (seen at 3 in FIGS. 1 and 2) will remain substantially the same, even if the resistances of the two legs are unknown (and possibly unequal). This feedback control is enabled by the design of the device because the pinching channels allow for confinement of the sample at the switching region even when there is zero current on one of the legs, as illustrated in FIG. 6.

Feedback control is achieved using an electrical circuit that controls and applies voltages and currents to electrodes connected to reservoirs of the device. The electrical circuit may include semiconductor and/or electromechanical devices used as switches. The switches may be used in linear (proportional) and/or non linear (ON/OFF) modes of operation. The electrical circuit may be computer controlled so that the magnitude of the applied voltages and currents, and the timing of their application, are specified by a computer algorithm, which may also be driven by the signal from the detector. The computer system may additionally be used to display, process, analyze, and store information gathered as a result of the operation of the device.

Using the device, fragments of a specific size may be isolated from an initial sample having a wide size distribution. For many applications, the goal is to isolate a band of narrow size distribution in the collection well. However, for other applications, a wider size distribution may be desired or tolerated in exchange for collection of more mass. As can be seen in FIG. 1, collection well 5 is not necessarily the terminus of the electrical circuit. Therefore, material entering collection well 5 will continue to electrophorese towards reservoir 10, eventually passing out of the collection well. In this way, the size of collection well 5 influences the maximum amount of material that can be collected since the smallest, fastest moving fragments will eventually leave the collection well as larger, slower fragments continue to enter.

The amount of material that can be collected may be increased by increasing the size of the collection well, by making this well the terminus of the electrical circuit, or by using a higher conductivity (or higher viscosity, or increased sieving) buffer in collection well 5. This will be possible if the sieving matrices in the channels are cross-linked or gelled. In this case, the collection well will be defined as a "hole" in the matrix that can be filled with a different buffer. When the collection buffer (the buffer in the collection well) is a higher conductivity than the running buffer (the buffer in the collection leg), material entering the well will concentrate and slow down (i.e., become stacked). Thus, for example, if the collection buffer is twice the conductivity of the running buffer, then the capacity of the collection well will be doubled. Alternatively, other methods of stacking may be used, such as increasing the viscosity, increasing the sieving or decreasing the current density (by increasing the cross-sectional area at the collection well). The viscosity may be increased by adding agents such as glycerol to the collection buffer. The sieving may be increased by adding polymers (such as PDMA) that impede the progress of the separated molecules.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A device for isolating one or more sample components of a sample material following separation of the sample material into a plurality of sample components, comprising:
   first and second pinching channels, each pinching channel having a first end and a second end;
   a separation channel extending between the first and second pinching channels, the separation channel having a first end and a second end;
   a collection leg having a first end and a second end;
   a collection well disposed in the collection leg between the first and second ends of the collection leg;
   a waste leg having a first end and a second end; and
   a switching region having an inlet end and an outlet end;
   wherein the second end of each of the first pinching channel, the second pinching channel, and the separation channel are in fluid communication with the inlet end of the switching region, and wherein the first end of the collection leg and the first end of the waste leg are in fluid communication with the outlet end of the switching region.

2. The device of claim 1 further comprising:
   a first buffer reservoir, a first waste reservoir, and a second waste reservoir, wherein the first end of the separation channel is in fluid communication with the first buffer reservoir, the second end of the collection leg is in fluid communication with the first waste reservoir, and the second end of the waste leg is in fluid communication with the second waste reservoir.

3. The device of claim 2, wherein the first end of the first pinching channel and the first end of the second pinching channel are in fluid communication with the first buffer reservoir.

4. The device of claim 2 further comprising:
   a second buffer reservoir and a third buffer reservoir, wherein the first end of the first pinching channel is in fluid communication with the second buffer reservoir and the first end of the second pinching channel is in fluid communication with the third buffer reservoir.

5. The device of claim 1 further comprising:
   a sieving matrix disposed in the separation channel.

6. The device of claim 1 further comprising:
   a loading well disposed in the separation channel.

7. The device of claim 1 further comprising:
   a sieving matrix disposed in the collection leg.

8. The device of claim 1, wherein a cross-sectional dimension of the separation channel is greater than a cross-sectional dimension of the switching region.

9. A system for isolating one or more sample components of a sample material following separation of the sample material into a plurality of sample components, comprising:
   a first device comprising first and second pinching channels, a separation channel extending between the first and second pinching channels, a collection leg, a waste leg, and a switching region, the collection leg including a collection well disposed in the collection leg between a first end and a second end of the collection leg, wherein the first and second pinching channels and the separation channel are in fluid communication with an inlet end of the switching region, and the collection leg and the waste leg are in fluid communication with an outlet end of the switching region;
   a detector in sensory communication with the device;
   a fluid direction system; and
   a processor operably coupled to the detector and the fluid direction system.

10. The system of claim 9, wherein the fluid direction system is configured to control movement of one or more sample components from the separation channel into one of the collection leg and the waste leg.

11. The system of claim 9 further comprising:
a second device comprising first and second pinching channels, a separation channel extending between the first and second pinching channels, a collection leg, a waste leg and a switching region, the collection leg including a collection well disposed in the collection leg between a first end and a second end of the collection leg, wherein the first and second pinching channels and the separation channel are in fluid communication with an inlet end of the switching region, and the collection leg and the waste leg are in fluid communication with an outlet end of the switching region.

12. The system of claim 11, wherein the fluid direction system is configured to simultaneously control movement of one or more sample components in the first device and one or more sample components in the second device.

13. The system of claim 12, wherein the fluid direction system is configured to control movement of the one or more sample components in the first device and the one or more sample components in the second device based on information received by the detector in a parallel circuit.

* * * * *